United States Patent
Kleibohmer et al.

(10) Patent No.: US 6,884,223 B2
(45) Date of Patent: Apr. 26, 2005

(54) METHOD FOR DETECTING α-OXOALDEHYDES IN THE WHOLE BLOOD, BLOOD PLASMA AND/OR SERUM OF A PATIENT

(75) Inventors: Wolfgang Kleibohmer, Münster (DE); Uta Schulze-Pellengahr, Ascheberg (DE)

(73) Assignee: Institut fur Chemo-und Biosensorik Munster E.V., Munster (DE)

( * ) Notice: Subject to any disclaimer, the term of this patent is extended or adjusted under 35 U.S.C. 154(b) by 0 days.

(21) Appl. No.: 10/297,424

(22) PCT Filed: May 29, 2001

(86) PCT No.: PCT/EP01/06101

§ 371 (c)(1), (2), (4) Date: Jan. 17, 2003

(87) PCT Pub. No.: WO01/94942

PCT Pub. Date: Dec. 13, 2001

(65) Prior Publication Data

US 2003/0176805 A1 Sep. 18, 2003

(30) Foreign Application Priority Data

Jun. 9, 2000 (DE) ........................................ 100 28 548

(51) Int. Cl.⁷ ................................................ A61B 5/08
(52) U.S. Cl. ........................ 600/532; 600/529; 73/23.3; 422/84
(58) Field of Search ................................. 600/300, 322, 600/348, 529–543; 73/23.3; 422/83–85, 50, 51, 61, 68.1, 9.1, 9.6, 9.7, 9.8; 436/815, 900, 128

(56) References Cited

U.S. PATENT DOCUMENTS

| 3,792,272 | A | * | 2/1974 | Harte et al. ................. 250/343 |
| 5,174,959 | A | * | 12/1992 | Kundu et al. ................. 422/59 |
| 5,601,079 | A | * | 2/1997 | Wong et al. ................. 600/322 |
| 5,618,734 | A | * | 4/1997 | Niwa et al. ................. 436/173 |
| 6,467,333 | B2 | * | 10/2002 | Lewis et al. ............... 73/31.05 |
| 6,620,107 | B2 | * | 9/2003 | Payne et al. ................ 600/532 |

FOREIGN PATENT DOCUMENTS

| DE | 219 287 A1 | 2/1985 | |
| DE | WO 2003/062459 A3 | * 7/2003 | ............ C12Q/1/32 |
| GB | WO 98/39470 | * 9/1998 | ............ C12Q/1/04 |
| WO | WO 98/57145 | 12/1998 | |
| WO | WO 98/56790 | 11/1999 | |

* cited by examiner

Primary Examiner—Mary Beth Jones
Assistant Examiner—Patricia C. Mallari
(74) Attorney, Agent, or Firm—Barnes & Thornburg

(57) ABSTRACT

A method for detecting α-oxoaldehydes in the whole blood, blood plasma and/or serum of a patient. A respiratory air sample is analyzed for the presence of at least one α-oxoaldehyde, and the presence of α-oxoaldehydes in the whole blood, blood plasma and/or serum of the patient is determined from the results of the analysis.

20 Claims, 4 Drawing Sheets

Figure 1:
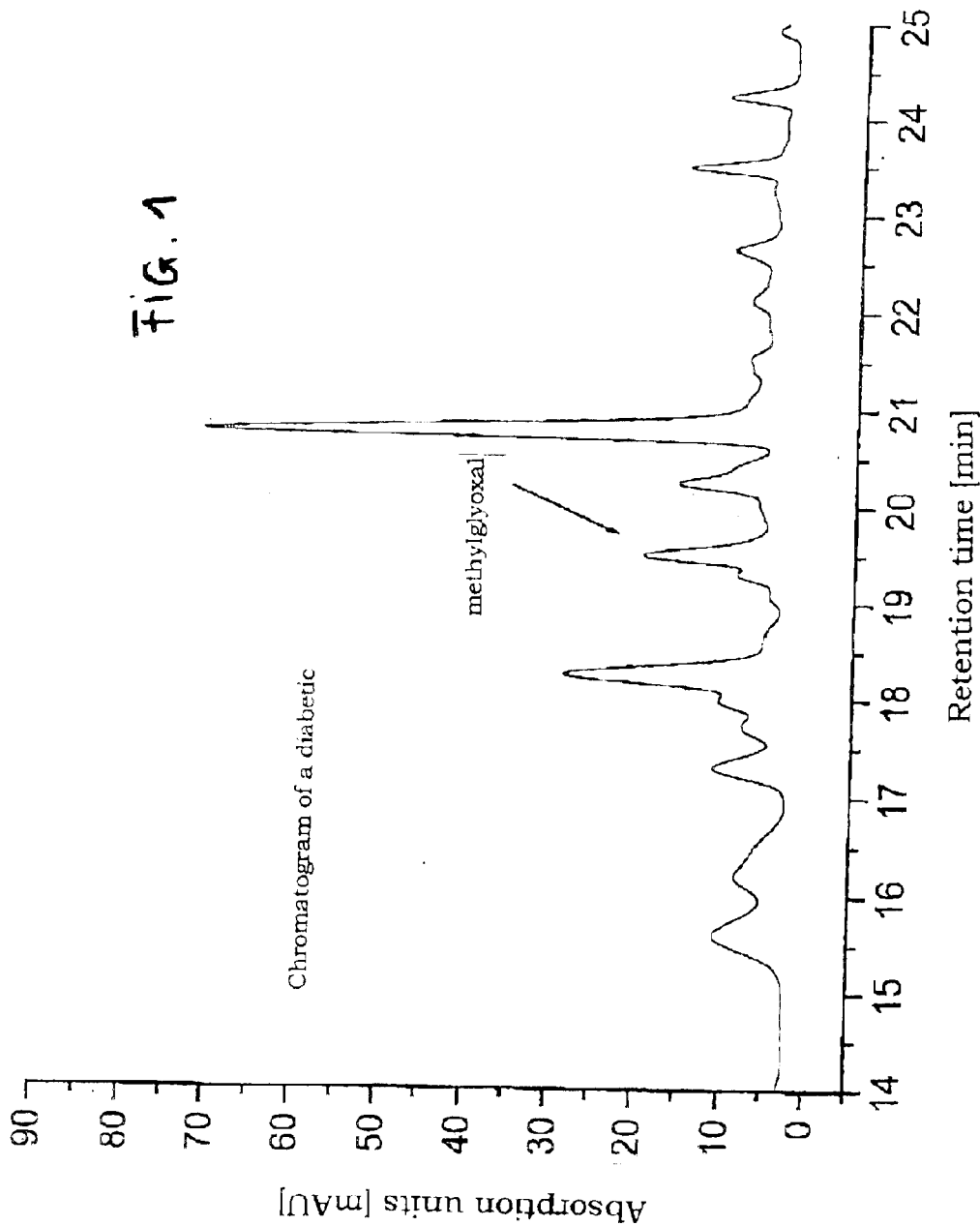

METHOD FOR DETECTING α-OXOALDEHYDES IN THE WHOLE BLOOD, BLOOD PLASMA AND/OR SERUM OF A PATIENT

CROSS-REFERENCE TO RELATED APPLICATIONS

This application is a U.S. national counterpart application of international application serial no. PCT/EP01/06101 filed May 29, 2001, which claims priority to German application serial No. 100 28 548.1 filed Jun. 9, 2000.

The present invention relates to a method for detecting α-oxoaldehydes in whole blood, in the blood plasma and/or in the serum of patients.

Complications arising as a result of long-standing diabetes diseases, i.e. insulin-dependent or non-insulin-dependent diabetes, such as kidney damage or clouding of the lenses of the eye, can only be detected with difficulty and often only at a late stage. Joint responsibility for these complications and consequential illnesses often lies with reactive metabolic products which, together with collagen, enzymes or other cellular components, form glycolates and can act as cell toxins by means of this mechanism. Corresponding markers for this disease can be detected according to the state of the art only via complex blood analytics in the laboratory.

In the last three to four years, experiments for elucidating the consequential illnesses in the course of long-standing diabetes have shown that the cytotoxic α-oxoaldehydes play an important and causal role (Beisswenger et al. (1999) Diabetes, Volume 48, p. 198–202). Hence in this connection, in particular the role of α-oxoaldehydes such as methylglyoxal, glyoxal or 3-deoxyglucuron is discussed. These materials are formed in the red blood corpuscles and occur in very small concentrations in the whole blood, in the blood plasma and in the serum.

In this connection, the α-oxoaldehyde methylglyoxal is of particular interest. Methylglyoxal can arise from triose phosphate, the metabolisation of ketone bodies and also during the metabolisation of threonine and is broken down further by means of glyoxalase. Methylglyoxal then reacts with proteins with the formation of imidazolone derivatives and bis-lysyl crosslinkings. This crosslinking of the proteins can lead to stabilisation of collagen and as a result to the thickening of membranes. Hence, these reactions explain at least part of diabetic complications, such as kidney failure and lens clouding.

The unaccompanied blood sugar determination, as is normal to date in the case of diabetics, gives no direct conclusion as to the momentary methylglyoxal concentration in the whole blood, in the plasma or in the serum.

According to the state of the art, the determination of α-oxoaldehydes is hence effected exclusively invasively, i.e. from the blood plasma. In the case of patients with insulin-dependent diabetes, there could be detected by Thornally, P. J., "Advanced Glycation and the development of diabetic complications. Unifying the involvement of glucose, methylglyoxal and oxidative stress" Endocrinology and Metabolism, 1996, 3, 149–166, a methylglyoxal concentration directly in the plasma which was five to six times higher compared to healthy comparative experimentees and two to three times higher in the case of patients with insulin-dependent diabetes. Alternatively, a determination of α-oxoaldehyde would be possible in the urine, but is not described in the literature, since the physiologically conditioned very low concentrations in the urine which are to be expected, would require too high an analysis complexity. Hence a direct determination of the α-oxoaldehydes in the plasma is required.

As a result of these examination methods according to the state of the art, regular checks and a possible needs-orientated dosing of medicines for targeted reduction of α-oxoaldehydes, such as methylglyoxal, in the whole blood, blood plasma and serum are very expensive.

WO 98/57 145 A1 describes a method for early detection of biological conditions, such as illnesses, by means of the analysis of suitable gaseous samples.

WO 99/56 790 A2 describes a diagnostic kit for implementation of breath tests which are used for diabetic diagnosis.

DD 219 287 A1 describes a measuring apparatus for checking blood sugar in the case of diabetics based on selective determination of the concentration of acetone in the breath gas on the basis of the radiation absorption using a measuring cuvette, filters, lenses and a power supply unit.

These methods according to the state of the art are consequently very complex and expensive and therefore have not been suitable to date for a regular routine check for determining the α-oxoaldehyde content in the whole blood, blood plasma or serum.

The object of the present invention is therefore to make available a method for detecting α-oxoaldehydes in the whole blood, blood plasma and/or serum of a patient which can be implemented in a simple, economical and reliable manner.

This object is achieved by means of a method with the features of claim 1. Advantageous developments of the method according to the invention are given in the dependent claims.

The method according to the invention is based on the fact that for instance an examination is not performed on the patient himself but merely a breath air sample (i.e. breath gas and/or breath condensate) of the patient is examined. With this method, α-oxoaldehydes are also detected in the breath air. Obviously α-oxoaldehydes, which are present mainly in the blood plasma, can in addition easily pass through a membrane, so that these can be detected in the breath gas or in the breath condensate. Furthermore, in contrast to other known markers, such as acetone, they are metabolically specific and do not occur ubiquitously in air. Hence, a simple, economical and reliable, regular and non-invasive monitoring of the α-oxoaldehyde formation in the whole blood, blood plasma and serum is possible in the case of diabetics so that, by means of suitable medication, the risk of possible consequential illnesses of diabetes can be reduced. Hence, the possibility exists, in the case of patients with long-standing diabetes, of introducing new strategies for avoidance of diabetic complications. For example, it is possible that the concentration of α-oxoaldehydes in the blood can be reduced by administering so-called scavenger compounds. Therapies of this type are supported by the non-invasive test method according to the invention and are possible on a merely routine basis.

Taking of the sample can be effected either by means of blowing into a corresponding sampling bag and/or suitable sample containers or by directing the breath air through an impinger. This impinger can be filled with a derivatisation medium for direct detection (by means of fluorescence or photometrically) or for a chromatographic determination. The filling of the impingers with reagents for electrochemical, spectrometric (e.g. IR spectrometric), enzymatic or immunochemical detection is also possible.

One detection method resides in the enzymatic conversion of methylglyoxal with glyoxalase into lactate and the subsequent determination of lactate with a modified sensor.

It is thereby important in the present invention, that all the components of a breath air sample, i.e. both the breath air and the breath condensate, are suitable for analysis of the α-oxoaldehyde content.

An example of the method according to the invention is described subsequently.

In this example, a breath air sample of a female patient with Type II diabetes was taken and examined for the α-oxoaldehydes glyoxal and methylglyoxal. The DNPH method according to Zurek et al., Analyst 1999, Vol. 124, p. 1291–1295, was used as examination method.

The sampling of the breath air was implemented as follows: via a mouthpiece with a tube, a sample bag (here a Tedlar® bag) with a volume of 30 litres was blown into by the test person/patient.

The sampling via a Tedlar bag was implemented in order subsequently to be able to conduct a defined volume across the collection phase.

Subsequent to the sampling, a defined air volume (20 l in the case of a volume flow <2 l/min) was sucked by means of a pump out of the bag via a cartouche which contains the collected material. The commercially available cartouche was filled with silica gel covered with 2,4-dinitrophenylhydrazine (Supelco: article no. 505358) as collected material. The α-oxoaldehydes reacted according to the following equation into 2,4-dinitrohydrazones and were retained on the silica gel.

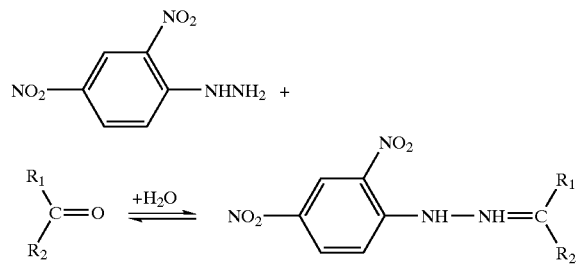

The resultant derivatives were subsequently eluted with 4 ml of acetonitrile from the cartouche and the obtained eluate was reduced to dryness. The remaining residue was dissolved again with 500 µl of acetonitrile. An aliquot of 20 µl was transferred into the HPLC system for analysis.

An HPLC method according to the principle of reversed phase chromatography was used for analysis, with the following methodical parameters:
Column: Hypersil BDS C18, column length 10 cm, column diameter: 4 mm, particle size: 3 µm
Mobile phase: a mixture of acetonitrile and water, volume flow of 0.5 ml/min
Starting conditions: a mixture of acetonitrile and water (50:50; volume ratios)
Gradient: constant starting conditions over 10 minutes, then within 27 minutes to a volume proportion of acetonitrile of 100%. The data were detected by means of UV detection at 360 and 404 nm and recorded with a Hewlett Packard Chem-Station.
FIG. 1:
In order to protect the identification of the substances, a part of the eluate of the collection cartouche was analysed under the above-described conditions with an HPLC system, which in addition to the UV detector had a mass-spectrometric detector available (FIG. 1). The latter permits the identification of the substances by means of their molecular mass and also by means of the disintegration of the molecule into characteristic molecular fragments.

Figure 2:
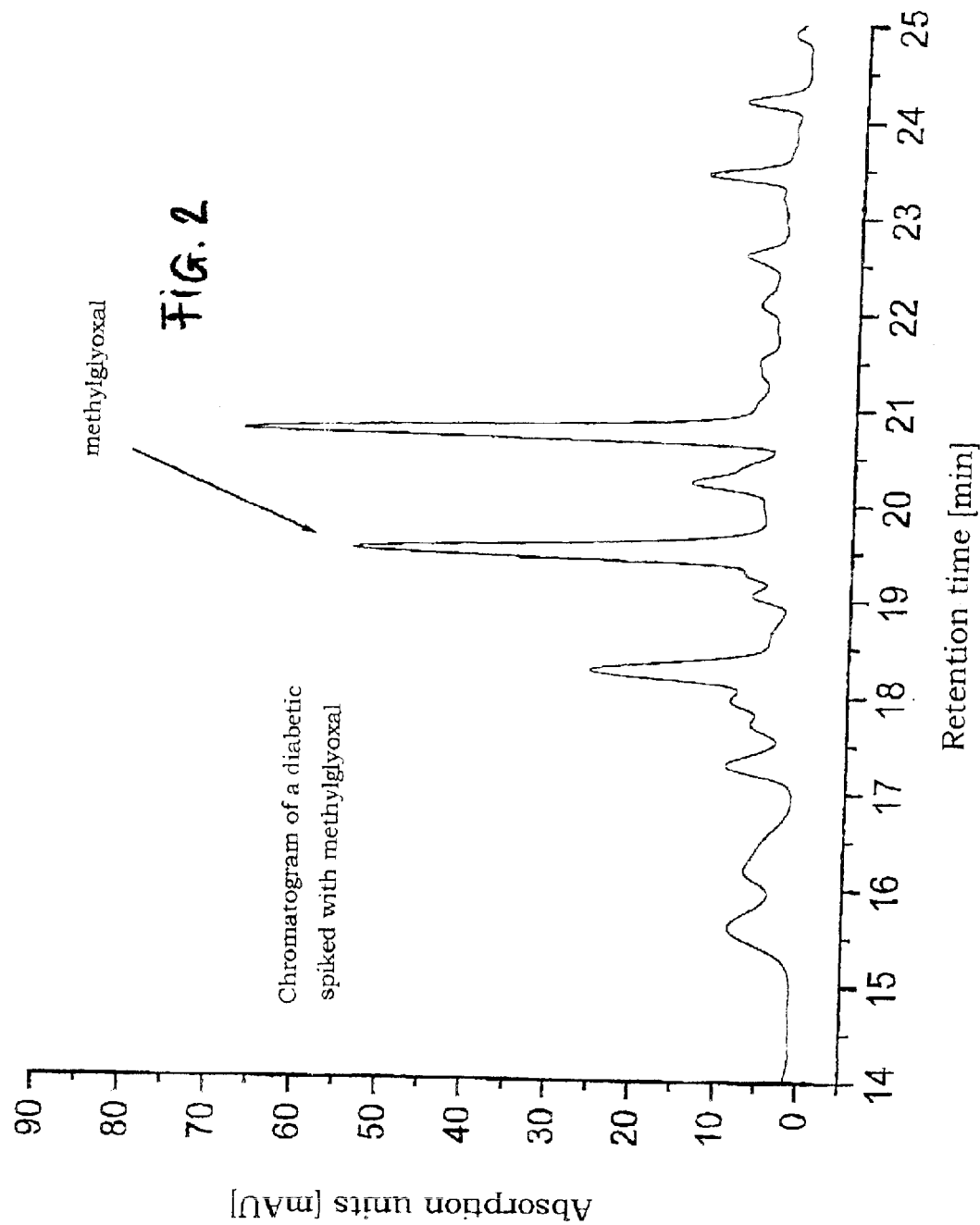

Defined quantities of the derivatives of the α-oxoaldehydes were added to a further part of the eluate and the solution was analysed by means of HPLC and UV detection (principle of standard addition) (FIG. 2). Dependent upon the added quantity of derivative, the corresponding signal of the compound in the chromatogram is increased and thus the identification is confirmed.

In FIG. 1, the peak for acetone and the peak for methylglyoxal can immediately be detected. Hence, it is shown that the metabolic product methylglyoxal can be detected also in the breath air sample and hence non-invasively and immediately indicates, on the basis of a metabolic specificity, the presence of methylglyoxal in the blood plasma of the patient. Since methylglyoxal does not occur ubiquitously, distortions of the measurements and falsifications of the measurement results due to the surroundings of the patient are not to be expected.

During further comparative tests with healthy comparative experimentees, no α-oxoaldehyde was able to be detected to date in their breath air.

Figure 3:
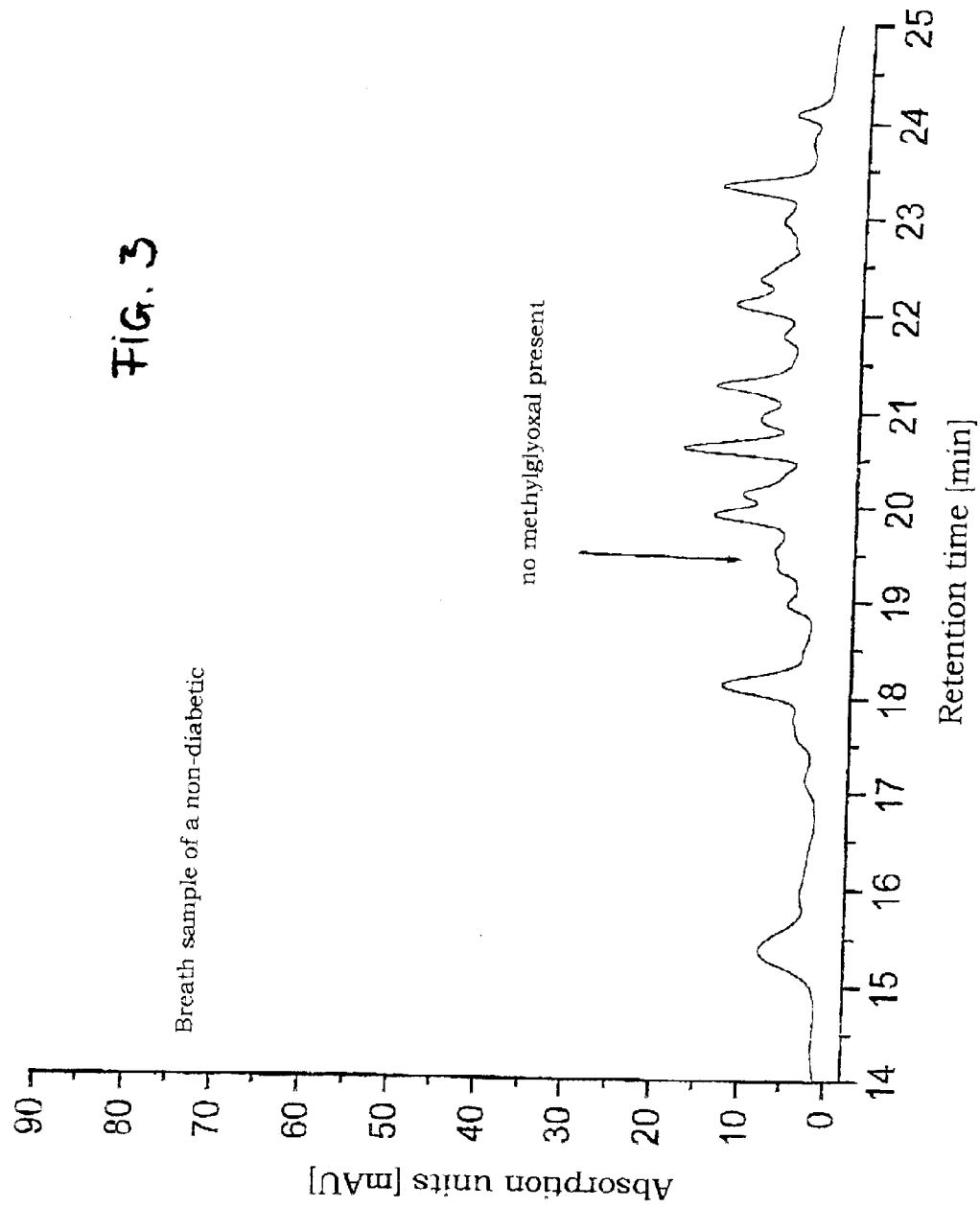
Figure 4:
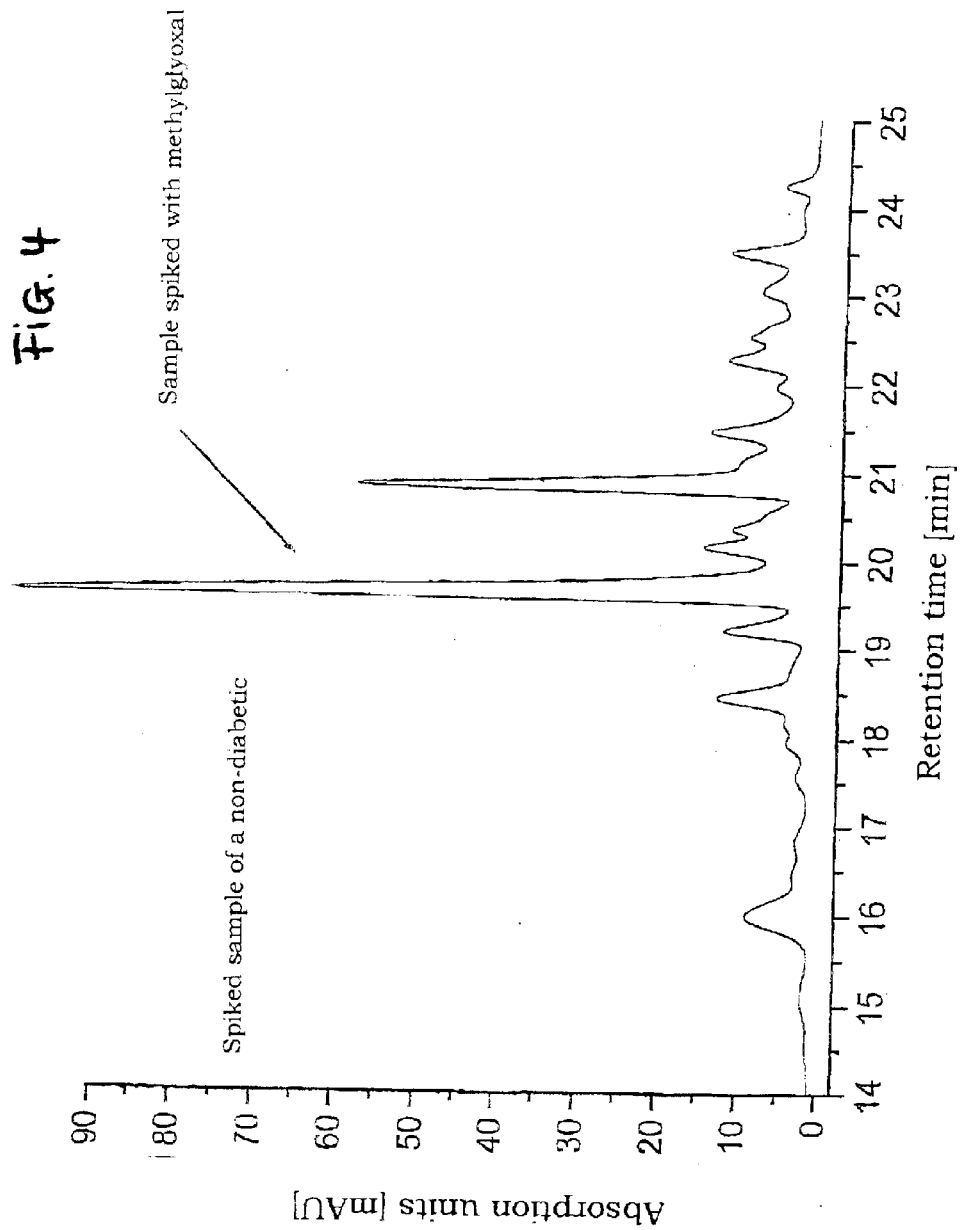

As an example, the breath air samples of healthy comparative experimentees were examined corresponding to the above-described method. FIG. 3 shows the resultant chromatogram for a healthy experimentee. No evaluable signal can be detected in the retention time region of the α-oxoaldehydes. After addition of a methylglyoxal standard a signal appeared in 19.50 minutes in the chromatogram, as is shown in FIG. 4.

What is claimed is:

1. A method for detecting α-oxoaldehydes in at least one of whole blood, blood plasma and serum of a patient, the method comprising analyzing a breath air sample for the presence of at least one α-oxoaldehyde and deducing the presence of α-oxoaldehydes in the at least one of whole blood, blood plasma and serum of the patient from the analysis result.

2. The method according to claim 1 wherein analyzing a breath air sample for the presence of at least one α-oxoaldehyde includes derivatizing the at least one α-oxoaldehyde in the breath air sample by means of a derivatization medium and determining the resulting derivatives.

3. The method according to claim 2 wherein determining the resulting derivatives includes determining the resulting derivatives by one of the following methods fluorometrically; photometrically; and, chromatographically.

4. The method according to claim 1 wherein analyzing a breath air sample for the presence of at least one α-oxoaldehyde includes at least one of enclosing the breath air sample in a sample bag, enclosing the breath air sample in another suitable sample container and directing the breath air sample through an impinger.

5. The method according to claim 4 wherein analyzing a breath air sample for the presence of at least one α-oxoaldehyde includes derivatizing the at least one α-oxoaldehyde in the breath air sample by means of a derivatization medium and determining the resulting derivatives.

6. The method according to claim 1 wherein analyzing a breath air sample for the presence of at least one α-oxoaldehyde and deducing the presence of α-oxoaldehydes in the at least one of whole blood, blood plasma and serum of the patient from the analysis result includes converting methylglyoxal which is contained in the breath air sample into lactate with glyoxalase and subsequently detecting the lactate with a sensor.

7. The method according to claim 1 wherein analyzing a breath air sample for the presence of at least one α-oxoaldehyde includes detecting the α-oxoaldehydes by at least one of the following methods: electrochemically; spectrometrically; enzymatically; and, immunochemically.

8. The method according to claim 1 wherein analyzing a breath air sample for the presence of at least one α-oxoaldehyde includes determining the α-oxoaldehydes in the breath air sample mass-spectrometrically.

9. The method according to claim 1 wherein analyzing a breath air sample for the presence of at least one α-oxoaldehyde includes determining the concentration of α-oxoladehydes in the breath air sample, and deducing the presence of α-oxoaldehydes in the at least one of whold blood, blood plasma and serum of the patient includes deducing the concentration of α-oxoaldehydes in the at least one of whole blood, blood plasma and serum of the patient therefrom.

10. The method according to claim 9 wherein analyzing a breath air sample for the presence of at least one α-oxoaldehyde includes analyzing a breath air sample for the presence of at least one of methylglyoxal, glyoxal and 3-deoxyglucuron.

11. The method according to claim 10 wherein analyzing a breath air sample for the presence of at least one α-oxoaldehyde includes at least one of enclosing the breath air sample in a sample bag, enclosing the breath air sample in another suitable sample container and directing the breath air sample through an impinger.

12. The method according to claim 11 wherein analyzing a breath air sample for the presence of at least one α-oxoaldehyde includes derivatizing the at least one α-oxoaldehyde in the breath air sample by means of a derivatization medium and determining the resulting derivatives.

13. The method according to claim 10 wherein analyzing a breath air sample for the presence of at least one α-oxoaldehyde includes derivatizing the at least one α-oxoaldehyde in the breath air sample by means of a derivatization medium and determining the resulting derivatives.

14. The method according to claim 9 wherein analyzing a breath air sample for the presence of at least one α-oxoaldehyde includes derivatizing the at least one α-oxoaldehyde in the breath air sample by means of a derivatization medium and determining the resulting derivatives.

15. The method according to claim 9 wherein analyzing a breath air sample for the presence of at least one α-oxoaldehyde includes at least one of enclosing the breath air sample in a sample bag, enclosing the breath air sample in another suitable sample container and directing the breath air sample through an impinger.

16. The method according to claim 15 wherein analyzing a breath air sample for the presence of at least one α-oxoaldehyde includes derivatizing the at least one α-oxoaldehyde in the breath air sample by means of a derivatization medium and determining the resulting derivatives.

17. The method according to claim 1 wherein analyzing a breath air sample for the presence of at least one α-oxoaldehyde includes analyzing a breath air sample for the presence of at least one of methylglyoxal, glyoxal and 3-deoxyglucuron.

18. The method according to claim 17 wherein analyzing a breath air sample for the presence of at least one α-oxoaldehyde includes at least one of enclosing the breath air sample in a sample bag, enclosing the breath air sample in another suitable sample container and directing the breath air sample through an impinger.

19. The method according to claim 18 wherein analyzing a breath air sample for the presence of at least one α-oxoaldehyde includes derivatizing the at least one α-oxoaldehyde in the breath air sample by means of a derivatization medium and determining the resulting derivatives.

20. The method according to claim 17 wherein analyzing a breath air sample for the presence of at least one α-oxoaldehyde includes derivatizing the at least one α-oxoaldehyde in the breath air sample by means of a derivatization medium and determining the resulting derivatives.

* * * * *